(12) United States Patent
Takai et al.

(10) Patent No.: US 6,361,638 B2
(45) Date of Patent: *Mar. 26, 2002

(54) PROCESS FOR PRODUCING A NONWOVEN FABRIC

(75) Inventors: Hisashi Takai, Kawanoe; Akira Shibata, Kagawa, both of (JP)

(73) Assignee: Uni-Charm Corporation, Ehime (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/256,656

(22) Filed: Feb. 23, 1999

Related U.S. Application Data (62) Division of application No. 08/890,466, filed on Jul. 8, 1997.

(30) Foreign Application Priority Data

Jul. 11, 1996 (JP) .............................................. 8-181755
Sep. 11, 1996 (JP) .............................................. 8-240378

(51) Int. Cl.⁷ ......................... A61F 13/15; B32B 27/14
(52) U.S. Cl. ..................... 156/209; 156/219; 156/220; 156/290

(58) Field of Search .................................. 428/174, 187, 428/195, 198; 442/337, 394, 409; 156/292, 290, 196, 209, 219, 220, 324

(56) References Cited

U.S. PATENT DOCUMENTS

| | | | | | |
|---|---|---|---|---|---|
| 5,342,343 | A | * | 8/1994 | Kitaoka et al. | 604/385 |
| 5,578,024 | A | * | 11/1996 | Mizutani et al. | 604/380 |
| 5,837,352 | A | * | 11/1998 | English et al. | 428/198 |
| 5,897,541 | A | * | 4/1999 | Uitenbrock et al. | 604/358 |

FOREIGN PATENT DOCUMENTS

WO    94/23107    * 10/1994

* cited by examiner

Primary Examiner—Sam Chuan Yao
(74) Attorney, Agent, or Firm—Koda & Androlia (57) ABSTRACT

In a fibrous web, press-welded line portions are formed, and press-welded dot portions are formed in portions other than the press-welded line portions. The formation of the press-welded line portions makes it possible to raise the surface of the fibrous web, to increase the bulkiness of the nonwoven fabric and to make the nonwoven fabric soft. Further, figures are drawn by the press-welded line portions, whereby the nonwoven fabric comes to have an excellent appearance in comparison to a conventional nonwoven fabric.

4 Claims, 4 Drawing Sheets

PROCESS FOR PRODUCING A NONWOVEN FABRIC

This application is a Division of Ser. No. 08/890,466 filed on Jul. 8, 1997.

BACKGROUND OF THE INVENTION

1. Field of the Invention

The present invention relates to a nonwoven fabric which is used in a disposable diaper, a sanitary napkin or kitchen utensils. More specifically, the present invention relates to a nonwoven fabric which has a solid, soft appearance, looks solid and soft and which can maintain a satisfactory bond strength of fibers, as well as to a process for producing the same.

2. Prior Art

There is a nonwoven fabric having a base weight of at least 15 $g/m^2$ and at most 45 $g/m^2$ which fabric is embossed to have a raised line pattern (embossed pattern). In this nonwoven fabric, fibers on the surface of the fibrous web formed of fluffed fibers are adhered relatively densely by a predetermined method, for example, by heat-welding or entangling, and the adhered portions are recessed. The embossed pattern has been provided through this adhesion.

Since, however, the embossed pattern is formed densely throughout this nonwoven fabric, the difference in height between the recessed portion given through this embossing and the other portion in the nonwoven fabric is small. Accordingly, the surface of the nonwoven fabric is less raised, that is, it has a less solid appearance. Consequently, it does not look soft, nor does it feel soft when one touches it.

Figure 9:
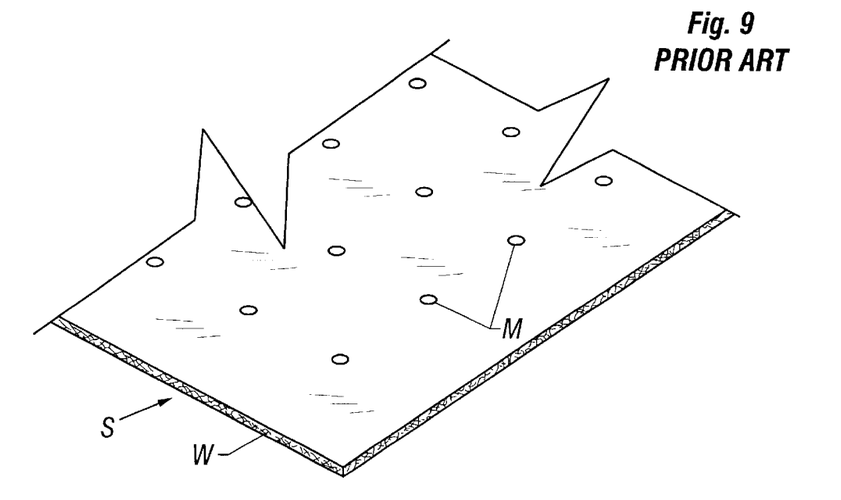
FIG. 9 is a perspective view showing the appearance of the conventional nonwoven fabric of this type.

Meanwhile, as shown in FIG. 9, in a product in which welded dot portions M are formed in a fibrous web W at a fixed pitch, a specific volume (volume/weight) is relatively large in the portions other than the welded portions M, and it can easily be given a solid appearance.

Nevertheless, in the product shown in FIG. 9, the area of the welded portion M is small, the outer periphery of each welded portion M is short, and the nonwoven fabric is less raised. Therefore, the difference in volume between the welded portion M and the surrounding portion is small, so that the raising of the nonwoven fabric is unsatisfactory. Thus, the pattern is monotonous, lacking variety when it is adhered to, for example, an outer surface of an outer film in a disposable diaper.

Further, a nonwoven fabric shown in FIG. 9 is laminated on the outer surface of the outer film in a disposable diaper or the like, and a resin film of the outer film and the nonwoven fabric are welded; this welded portion has a pattern or a figure. However, in case the nonwoven fabric having welded dot portions M as shown in FIG. 9 is further welded to the resin film, the portions welded to the resin film are overlapped with the welded dot portions M, and the area of the welded portions is larger than the area of the nonwoven fabric. Thus, the line pattern formed by the welded portions M lacks sharpness, and the nonwoven fabric does not look solid. Further, as the resin film and the nonwoven fabric are welded to each other in the welded portions M, these portions feel stiff. Further, when an air-permeable film is used as the resin film and patterned or figured welded portions are formed in the resin film and the nonwoven fabric, the air permeability of the resin film is reduced as a whole.

Besides the conventional nonwoven fabric is formed of an uncolored fibrous web in many cases. Even if it is formed of a colored web, the overall nonwoven fabric has a single color. For this reason, there is not a product which has a color contrast and in which a pattern is expressed upon using a bulkiness of the nonwoven fabric.

SUMMARY OF THE INVENTION

The present invention aims to solve the above-mentioned problems associated with the prior art. It is an object of the present invention to provide a nonwoven fabric which makes vivid a line pattern formed with press-welded portions by improving the shape of the press-welded portions, which can be rendered bulky by raising the non-press-welded portions, which looks soft and feels soft when touched with the hand, as well as a process for producing the same.

Another object of the present invention is to provide a nonwoven fabric which can have a pattern or a figure by improving the shape of the press-welded portions, for example, which can have a pattern or a figure in the outer surface when used as an outer sheet of a disposable diaper for babies or little children, which can increase a beautiful appearance and in which the presence or absence of urine in a diaper can visually be observed in the press-welded portions from outside the diaper, as well as a process for producing the same.

Still another object of the present invention is to provide a nonwoven fabric in which the shape of the press-welded portions is improved to make bulky the non-press-welded portions and the press-welded portions can provide a clearer pattern to give a color contrast, as well as a process for producing the same.

The present invention is to provide a nonwoven fabric having partially press-welded portions that are recessed in the surface of a fibrous web, characterized in that the press-welded portions have a continuous line or uncontinuous line (broken line) pattern with a curved or square part, and the portions other than the continuous line or uncontinuous line press-welded portions in the fibrous web have a raised pattern relative to the recess of the press-welded portions.

As the fibrous web which is a material of this nonwoven fabric, the web formed of relatively dense fibers having a base weight of at least 15 $g/m^2$ and at most 45 $g/m^2$ is preferably used. When the specific volume of the press-welded portions is at least 3 $cm^3/g$ and at most 10 $cm^3/g$ and the specific volume of the non-press-welded portions is at least 10 $cm^3/g$ and at most 30 $cm^3/g$, the non-press-welded portions in the fibrous web become bulky, and the boundary between the press-welded portions and the non-press-welded portions make clear and the nonwoven fabric comes to look solid.

The portion surrounded with the continuous line or uncontinuous line press-welded portions is formed in the above-mentioned non-woven fabric, and the fibrous web in the surrounded portion is preferably raised relative to the recessed press-welded portions.

It is further preferable to form a plurality of press-welded dot portions other than the continuous line or uncontinuous line press-welded portions. In this case, it is advisable that the press-welded dot portions are formed where these portions do not overlap with the continuous line or uncontinuous line press-welded portions of the fibrous web. The continuous line or uncontinuous line press-welded portions are preferably spaced apart from the adjacent press-welded dot portions by at least 1 mm, preferably at least 1 mm and at most 5 mm.

It is still further preferable that the total area of the press-welded dot portions in the nonwoven fabric is the same as, or less than, the total area of the continuous line or uncontinuous line press-welded portions.

It is furthermore preferable to use fibers having a square or uneven cross-section as a starting material of the fibrous web.

It is moreover preferable that a color sheet is overlaid on the reverse surface of the nonwoven fabric and they are adhered so that the color of the color sheet is seen through the press-welded portions of the nonwoven fabric. This procedure gives the sharp color contrast between the recessed press-welded portions of the fibrous web and the bulky portions of the fibrous web and makes clear the pattern drawn by the press-welded portions.

A process for producing a nonwoven fabric in the present invention comprises a step of forming a fibrous web from starting fibers, a step of feeding the fibrous web between a hot roller provided on the surface with curved or square line or uncontinuous line projected portions and a hot roller having a smooth surface, and a step of holding the fibrous web between the hot rollers provided on the surface with the projected portions and the hot roller having the smooth surface, and press-welding the fibers of the fibrous web with the projected portions on the surface of the hot roller to partially recess the fibrous web and form the press-welded portions.

A plurality of dot-shaped projected portions, in addition to the above-mentioned continuous or uncontinuous line projected portions are formed on the surface of the hot roller.

In a method of placing the color sheet under the nonwoven fabric and welding them, a colorless fibrous web is laminated on a dyed or colored thermoplastic sheet, the laminate is fed between the two hot rollers and held therebetween, and the thermoplastic sheet and the fibrous web are press-welded together with the projected portions formed on the surface of the hot roller to give press-welded portions.

In another method, a fibrous web formed of colorless fibers is laminated on a color fibrous web formed of dyed or colored fibers, the laminate of these fibrous webs is fed between the two hot rollers and held therebetween, and the color fibrous web and the colorless fibrous web are partially press-welded with the projected portions formed on the surface of the hot roller to give press-welded portions.

In this nonwoven fabric, the fibrous web is formed of thermoplastic short fibers having a fiber length of at least 30 mm and at most 70 mm, and fed to the hot rollers. When the fibrous web is passed through the hot rollers, it is partially pressed with the projected portions of one hot roller, and heated to give partially press-welded portions. In the present invention, it is assumed that the thermoplastic fibers of the fibrous web are not welded in the portions other than the above-mentioned press-welded portions. However, since the fibrous web may be raised on the portions other than the recesses in the press-welded portions of the fibrous web, the thermoplastic fibers of the fibrous web may be hot-welded in the portions other than the press-welded portions.

The press-welded dot portions formed with the projected portions of the hot roller refer to circular, elliptical or very short line press-welded portions. For example, circular-, elliptical- or very short line-shaped projected portions are formed on the surface of the hot roller at a fixed space. The press-welded dot portions refer to those in which the area of each of these portions is much smaller than that of each of the continuous line or uncontinuous line press-welded portions. The uncontinuous line press-welded portions refer to short line press-welded portions which are spaced apart from each other.

Figure 8:
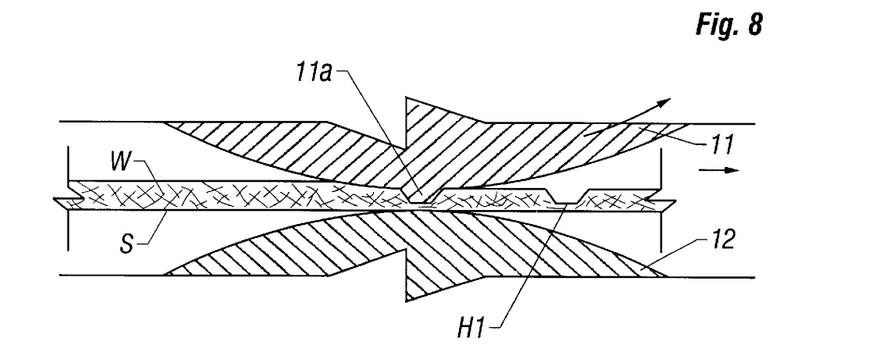
FIG. 8 is an enlarged view of a part of FIG. 7.

The press-welded portions are not only those recessed in one surface of the nonwoven fabric as shown in FIG. 8, but also those recessed in both surfaces of the nonwoven fabric.

Figure 3:
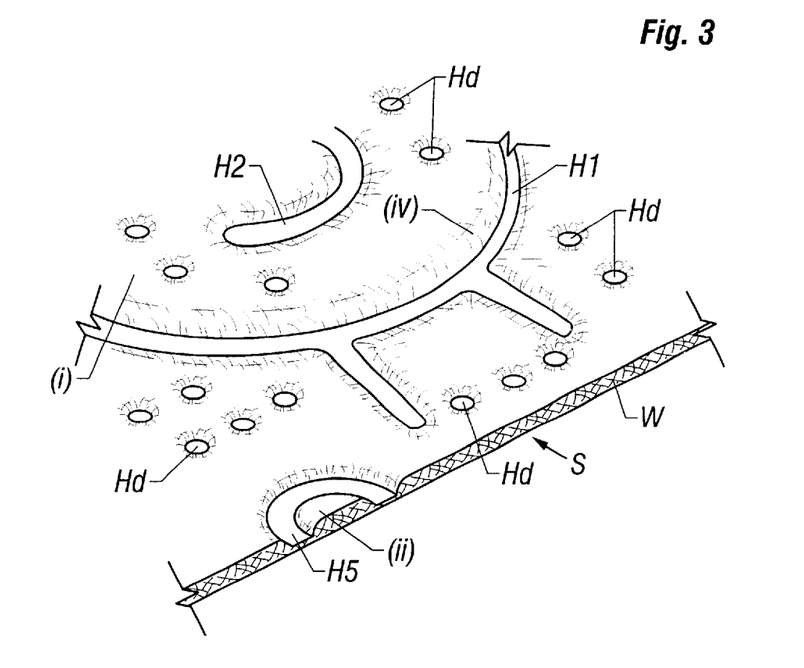
FIG. 3 is an enlarged perspective view of a part of a nonwoven fabric shown in FIG. 2.

The continuous line or uncontinuous line press-welded portions are formed in the nonwoven fabric of the present invention. The continuous line or uncontinuous line press-welded portions may be straight lines, but preferably curved lines (arcked lines) or square lines. When the continuous line or uncontinuous line press-welded portions are the straight lines, a pattern can be formed by crossing the straight line press-welded portions. When the press-welded portions are the continuous lines or the uncontinuous lines, the surface of the fibrous web is raised in the boundary between the press-welded portions and the non-press-welded portions, and the raised portions become conspicuous as shown in FIG. 3. Consequently, the overall nonwoven fabric becomes bulky and looks solid. It looks or feels soft compared to the conventional nonwoven fabric. In the continuous line or uncontinuous line press-welded portions, the fibers become filmy and transparent or semitransparent. Therefore, the color contrast between these press-welded portions and non-press-welded portions goes sharp. Thus, the continuous line or uncontinuous line press-welded portions look clear; the nonwoven fabric improves in the appearance as compared to the conventional nonwoven fabric.

Fibers having a cross-section shown in FIG. 4(A), (B) or (C) may be used as starting fibers of the fibrous web. The fibers having the above-mentioned cross-section reflect light diffusely to increase the whiteness of the fibrous web. Accordingly, the raised portions other than the press-welded portions come to have a clear white color. Meanwhile, the press-welded portions become transparent or semitransparent. Therefore, the contrast between the transparent or semitransparent press-welded portions and the raised white portions other than the press-welded portions is made even clearer.

In the present invention, the continuous line or uncontinuous line press-welded portions are made to have a curved or square shape to be able to provide a predetermined pattern. This pattern is given from the curved (arched) or square shape, or a combination thereof continuous line or uncontinuous line press-welded portions or a combination thereof. This pattern is provided by a figure, a combination of figures, characters, symbols, a combination of characters and symbols, a combination of figures and characters, and a combination of figures and symbols.

Figure 2:
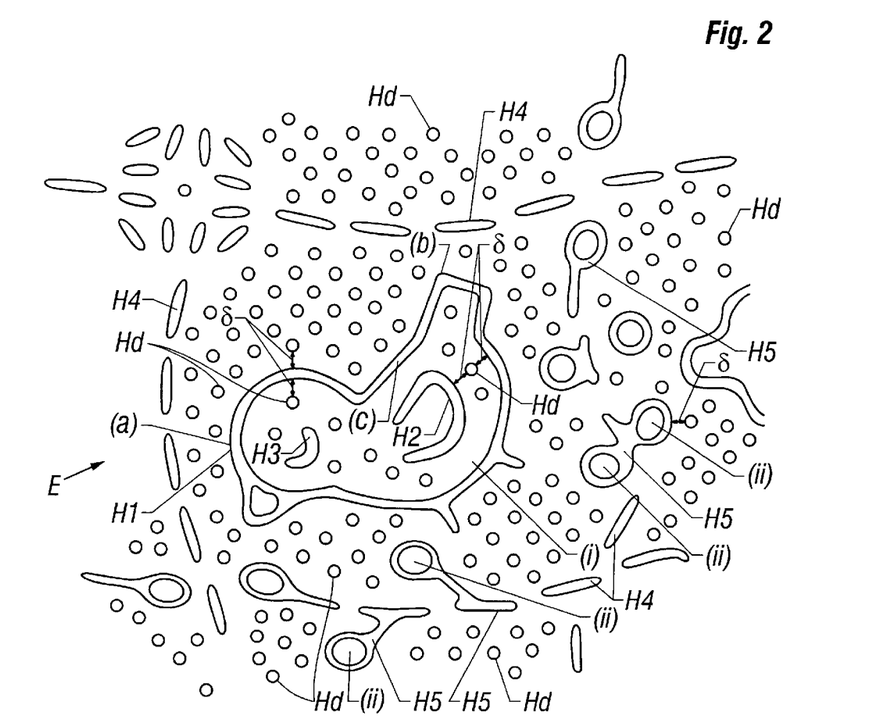
FIG. 2 is an enlarged plan of a part of a nonwoven fabric shown in FIG. 1.

As shown in an enlarged view of FIG. 2, when the fibrous web constituting the nonwoven fabric is partially press-welded in the production of the nonwoven fabric, the pattern (or the figure) is expressed from the press-welded portions to give an appearance different from that of the conventional nonwoven fabric shown in FIG. 9. The pattern is expressed from the continuous line or uncontinuous line press-welded portions. The surface of the fibrous web is raised from the continuous line or uncontinuous line press-welded portions, and the nonwoven fabric is bulky, solid and soft visually and tactually. Further, the contrast between the continuous line or uncontinuous line press-welded portions and the non-press-welded portions becomes clear, and the pattern is seen sharply.

Moreover, when a color sheet is adhered to the reverse surface of the nonwoven fabric having the press-welded portions, the color of the color sheet on the reverse surface appears through the transparent or semitransparent press-welded portions, and the sharp color contrast is given between the press-welded portions and the non-press-welded bulky portions. Especially when using fibers having a square or uneven sectional shape in the nonwoven fabric, the non-press-welded portions have a clear white color, making sharp the contrast between the color of the color sheet on the press-welded portions and the white color of the non-press-welded portions.

For example, a colored resin film is used as a color sheet. The colored resin film is adhered to the reverse surface of the nonwoven fabric having the press-welded portions that form the pattern. The nonwoven fabric having the pattern and the colored resin film may be adhered partially or wholly using a hot melt adhesive or another transparent adhesive.

It is also possible that the non-press-welded fibrous web is laminated on the colored thermoplastic resin film, the colored thermoplastic resin film and the fibrous web are press-welded together, and the colored resin film and the fibrous web are press-welded together in the press-welded portions.

When a resin sheet having a light warm color such as pink is used as the colored resin film, the nonwoven fabric looks softer. When using a resin sheet having a color such as light blue, a user can feel clean and fresh.

The nonwoven fabric of the present invention may have only curved or square continuous line or uncontinuous line (broken line) like press-welded portions and be free from press-welded dot portions. However, it is preferable that there are the above-mentioned plural press-welded dot portions besides the continuous line or uncontinuous line press-welded portions.

Further, portions surrounded by the curved or/and square continuous line or uncontinuous line press-welded portions are formed in the above-mentioned pattern. It is advisable that the above-mentioned plural press-welded dot portions are formed inside and outside the surrounded portions.

When the press-welded dot portions are formed inside and outside the surrounded portions other than the continuous line or uncontinuous line press-welded portions that give the pattern as mentioned above, it is possible to increase the tensile strength of the nonwoven fabric in the portions other than the continuous line or uncontinuous line press-welded portions, and also to prevent fluffing of the fibrous web in the portions other than the continuous line or uncontinuous line press-welded portions.

In the present invention, when forming the continuous line or uncontinuous line press-welded portions and the press-welded dot portions, it is advisable that these portions are provided so as not to overlap with each other. That is, as shown in FIG. 2, it is advisable that the press-welded dot portions are formed in spaced apart relationship with the continuous line or uncontinuous line press-welded portions at a fixed space (for example, at least 1 mm and at most 5 mm), and that the press-welded dot portions are formed in both sides of the continuous line or uncontinuous line press-welded portions at the same space. In this construction, the pattern drawn by the continuous line or uncontinuous line press-welded portions does not overlap with the press-welded dot portions, and it tends to become clear.

It is further advisable that the total area of the press-welded dot portions occupied in the nonwoven fabric is the same as, or less than, the total area of the continuous line or uncontinuous line press-welded portions occupied in the nonwoven fabric, whereby the pattern drawn by the continuous line or uncontinuous line press-welded portions is not erased by the press-welded dot portions, making it possible to make clear the pattern.

BRIEF DESCRIPTION OF THE DRAWINGS

FIGS. 4 (A), (B) and (C) are each a cross-sectional view of a starting fiber used in the nonwoven fabric of the present invention.

DETAILED DESCRIPTION OF THE PREFERRED EMBODIMENTS

Figure 1:
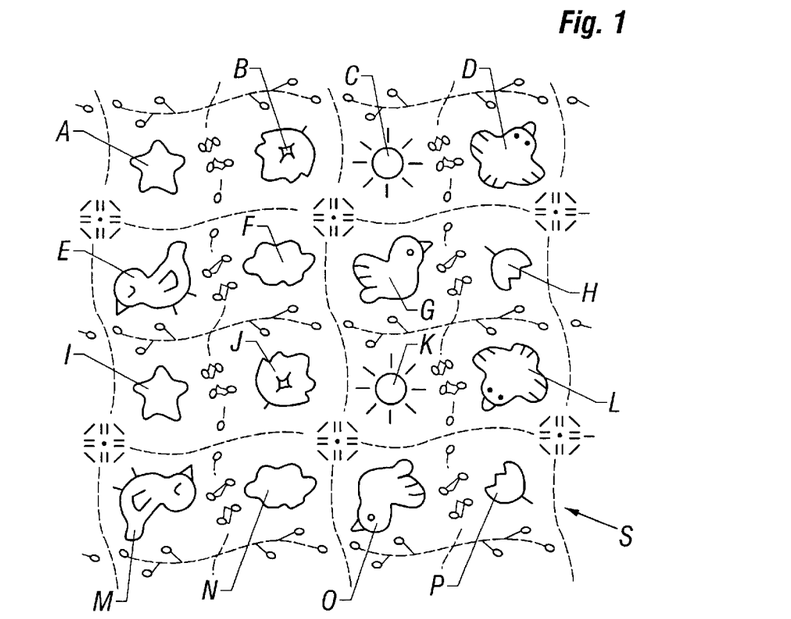
FIG. 1 is a plan of a part of a nonwoven fabric according to the present invention.

In a non-woven fabric S shown in FIG. 1, a fibrous web W formed of thermoplastic short fibers each having a length of from 30 mm to 70 mm is partially pressed and welded to form press-welded portions.

The fibrous web W is formed of thermoplastic fibers selected from polyethylene fibers and polypropylene fibers, or of a mixture of polyethylene fibers and polypropylene fibers. Or it is formed of composite fibers of a polyester and polyethylene, composite fibers of polypropylene and polyethylene, or a mixture of both composite fibers.

The above-mentioned press-welded portions comprise continuous line press-welded portions and press-welded dot portions which are formed at a fixed space. A design (figure) is expressed by the continuous line press-welded portions. This design comprises a combination of 9 patterns A to P in FIG. 1, and these 9 patterns are repeatedly formed in the flat surface of the nonwoven fabric S (fibrous web W).

FIG. 2 is an enlarged view of the pattern E in the nonwoven fabric S shown in FIG. 1.

In FIG. 2, the hatched portions are press-welded portions in which fibers of the nonwoven fabric are press-welded, and no fibers are welded in the other portions. Accordingly, the thickness of the non-press-welded portions of the nonwoven fabric is fixed, for example, 0.5 mm.

Portions indicated at Hd in FIG. 2 are press-welded dot portions, and the other welded portions are press-welded line portions. In the nonwoven fabric shown in FIG. 2, the continuous line press-welded portions are formed longer than the press-welded dot portions Hd.

Of the press-welded line portions, H1 has a curved shape (arched shape) (a), a square shape (b) and a straight line pattern (c). This press-welded portion H1 expresses a contour of a "chick". A fixed portion (i) is surrounded by this press-welded line portion H1. The press-welded line portion H2 expressing a "feather of a chick" and the press-welded line portion H3 expressing an "eye of a chick" are formed in this surrounded portion (i). Both of the press-welded line portions H2, H3 are curved.

The press-welded dot portions Hd are formed both inside and outside the portion (i) surrounded by the press-welded line portion H1. Besides, the press-welded line portions H1, H2, H3 and the press-welded dot portions Hd are formed where they do not overlap with each other. That is, as shown in FIG. 2, the space between the press-welded line portion H1 and the press-welded dot portions Hd which are situated inside the portion surrounded by H1 and the space between the press-welded line portion H1 and the press-welded dot portion Hd located outside the portion (i) surrounded by H1 are approximately the same (δ, for example between 1 mm and 5 mm) or more than δ. Likewise, with respect to the press-welded dot portions Hd between the press-welded line portions H1 and H2, the space between the press-welded dot portions Hd and press-welded line portion H1 and the space between the press-welded dot portions Hd and press-welded line portion H2 are equal to, or more than the space δ.

In addition, the outer periphery of the pattern "chick" expressed by the press-welded line portion H1 is surrounded in an approximately square shape by the press-welded line portions H4 which are approximately linear. This press-welded line portions H4 and the press-welded dot portions Hd do not overlap with each other. The space between the press-welded line portions H4 and press-welded dot portions Hd is equal to, or more than, the space δ.

The press-welded line portions H5 are also formed which surround the "chick" together with the press-welded line portions H4. The press-welded line portion H5 expresses a "flower", and is mainly made of a curved line. The press-welded line portion H5 forms the surrounded portion (ii) Since the area of the surrounded portion (ii) is small, the press-welded dot portions Hd are not formed inside the surrounded portion (ii). This press-welded line portions H5 are formed such that they do not overlap with the press-welded dot portions Hd. The space between the contour of the press-welded line portions H5 and the press-welded dot portion Hd is also equal to, or more than, the space δ.

Thus, in the nonwoven fabric S, the figures "chick", "surrounding line", "flower" and the like are expressed by the press-welded line portions H1, H2, H3, H4, H5, and the press-welded dot portions Hd are formed in the portions other than the press-welded line portions H1, H2, H3, H4, H5. The press-welded portions are surely spaced apart at the fixed space δ or at a space more than δ, whereby the portions in which thermoplastic fibers are not welded occupy at least a fixed area in the patterns A to P. Further, the press-welded dot portions Hd are distributed such that the volume ratio of the press-welded portions to the portions other than the press-welded portions is approximately fixed throughout the nonwoven fabric S.

In the patterns A, B, . . . in FIG. 1, the figures "star", "leaf", "sun", "cloud" and the like are drawn instead of the figure "chick". The relation between the press-welded line portions by which to draw these figures and the press-welded dot portions is the same as that in the pattern E shown in FIG. 2.

FIG. 3 is an enlarged view of a part of the press-welded line portions H1, H2, H5 shown in FIG. 2. In the press-welded line portions H1, H2, . . . , Hd, the fibrous web W formed of thermoplastic fibers is partially pressed and welded, and the thickness of the welded portions is smaller than that of the non-welded portion. In the press-welded portions, the nonwoven fabric is recessed in one surface. The thickness of the nonwoven fabric S in the press-welded portion is approximately 0.1 mm, and the specific volume thereof is at least approximately 3 $cm^3/g$ and at most 10 $cm^3/g$, for example, 4.3 $cm^3/g$. The thickness of the non-press-welded portions in the nonwoven fabric S is 0.5 mm, and the specific volume is at least approximately 10 $cm^3/g$ and at most 30 $cm^3/g$, for example, 21.7 $cm^3/g$.

The difference in the thickness between the press-welded portions and the non-press-welded portions of the nonwoven fabric S results in raising the surface of the fibrous web W (nonwoven fabric S) in the boundary therebetween. When the press-welded line portions (H1 and the like) are provided, the boundary line between the press-welded portions and the non-press-welded portions continuously extends long, and the raised portion on the surface of the fibrous web W (nonwoven fabric S) indicated at (iv) in FIG. 3 is continuously formed long. Accordingly, the portion (iv) looks raised in comparison to the surrounding press-welded dot portions Hd. Therefore, when the press-welded line portion is long, the overall nonwoven fabric looks raised and feels bulky when one touches it with the hand. For example, in FIG. 2, the press-welded line portion H1 which is a contour of the figure "chick" is long and surrounds the portion (i). Accordingly, in this surrounded portion (i), the shape "chick" looks raised from the overall surface of the nonwoven fabric S. Further, the surrounded portion (ii) having a small area is formed from the press-welded line portions H5 having the figure "flower". Since the press-welded line portion is not formed in this surrounded portions (ii), the fibrous web W (nonwoven fabric S) of this surrounded portions (ii) looks raised.

When the press-welded line portions H1, H2, H3, . . . extend long with a predetermined width, the raised portion on the surface of the fibrous web W becomes conspicuous in the boundary of the press-welded line portions, and looks bulky and soft as a whole.

In the press-welded line portions H1, H2, . . . and Hd, the thermoplastic fibers are pressed and hot-melted; these fibers are welded and become filmy. These press-welded line portions are transparent or semitransparent. Since the fibrous web has a high bulkiness in the non-press-welded portions, these portions have a white or semitransparent white color. The press-welded dot portions Hd are also filmy. However, since each of the press-welded dot portions Hd has a small area, the color contrast with the surroundings is not so clear. On the other hand, the press-welded line portions H1, H2, H3, H4, H5 are linear, and the transparent or semitransparent filmy portions extend long with a predetermined width. Consequently, the filmy press-welded line portions are conspicuous, and the color contrast between the press-welded line portions H1, H2, H3, H4, H5 and the other portions becomes clear. Since the contrast therebetween becomes clear, the figure "chick" provided by the press-welded line portion H1, the square of the press-welded line portions H4 that surrounds this figure and the figure "flower" provided by the press-welded line portions H5 look clear.

Figure 4:
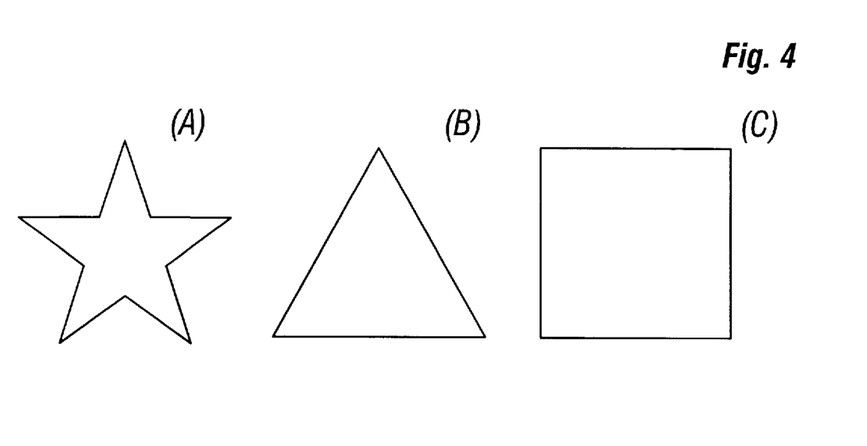

When a fiber having a star-like, triangular or square cross-sectional shape shown in (A), (B) or (C) of FIG. 4 is used as the starting fiber of the fibrous web, the difference between the press-welded line portions H1, H2, . . . and the non-press-welded portions can be made even clearer. When light is applied to the fiber having the cross-sectional shape shown in (A), (B) or (C) of FIG. 4, the light is reflected diffusely on the surface of this fiber, and the fibrous web W formed of this fiber comes to have a clear white color. Consequently, the non-press-welded raised portions of the nonwoven fabric S come to have a clear white color, and are sharply contrasted with the transparent or semitransparent filmy press-welded line portions H1, H2, . . . As a result, the figures formed by the press-welded portions H1, H2, . . . become conspicuous.

The press-welded line portions H1, H2, . . . and the press-welded dot portions Hd are arranged such that these two types of the portions do not overlap with each other, and they are spaced apart from each other at a predetermined space of □ or more. Consequently, it does not happen that the patterns expressed with the press-welded line portions H1, H2, . . . are hidden by the press-welded dot portions Hd. Since the press-welded dot portions Hd are formed at a fixed space where the press-welded line portions H1, H2, . . . are not formed, the thermoplastic fibers can surely be kept not to come out from the overall nonwoven fabric S, making it possible to prevent the fluffing of the fibrous web W (nonwoven fabric S).

In order to make the figures drawn by the press-welded line portions H1, H2, H3, . . . much clearer than the press-welded dot portions Hd, it is advisable that the areas of the press-welded line portions H1, H2, H3, . . . that give the figures are the same as, or larger than, the areas of the press-welded dot portions Hd. The total area of the press-welded line portions H1, H2, H3, . . . and Hd is preferably at least 10% and at most 35%, more preferably at least 15% and at most 25% based on the area of the surface of the nonwoven fabric S. The formation of the press-welded portions at such an area ratio helps to secure the strength of the nonwoven fabric S, to prevent fluffing of the fibrous web (nonwoven fabric S), to make the figures approximately clear and to maintain the air permeability of the nonwoven fabric S.

Figure 5:
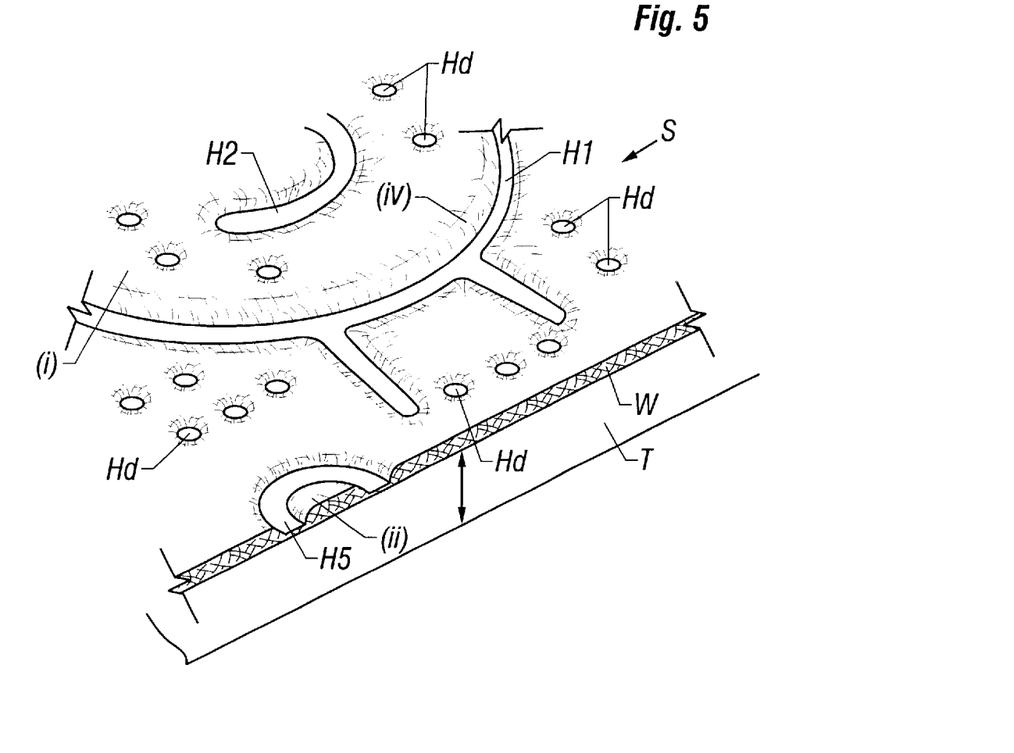
FIG. 5 is a perspective view of the nonwoven fabric shown in FIG. 4 under which a color sheet is placed.

For the figures drawn by the press-welded line portions H1, H2, H3 . . . to be made even clearer, it is advisable to overlay a color resin sheet on the reverse surface of the nonwoven fabric S and adhere them after the production of the nonwoven fabric S having the press-welded line portions. FIG. 5 illustrates a state where a color sheet T is put under the nonwoven fabric S. Since the press-welded line portions H1, H2, H3 . . . are transparent or semitransparent, the color of the color sheet is seen through the reverse surface of the nonwoven fabric S in the press-welded line portions H1, H2, H3, . . . , and the press-welded line portions H1, H2, H3, . . . look colored. Meanwhile, the portions other than the press-welded line portions are white because of the high bulkiness of the fibrous web W (nonwoven fabric S), and the color of the color sheet T is hardly seen therethrough. As a result, the contrast between the press-welded line portions H1, H2, H3, . . . through which the color of the color sheet T is seen and the white portions other than the press-welded line portions is much sharper, and the figures are rendered clearer.

In this case, various color sheets are available as the color sheet T. The color sheet T may be a colored resin film or a nonwoven fabric S formed of dyed or colored fibers. For example, when a color sheet T having a warm color such as light pink is used, a soft impression can be given to a user owing to the color which is seen through the press-welded portions. When using a blue color, a clean or fresh impression can be given.

In a method of adhering the color sheet T to the reverse surface of the nonwoven fabric S, a hot melt adhesive is spirally coated on the reverse surface of the nonwoven fabric S or/and the surface of the color sheet T, and the nonwoven fabric S and the color sheet T are adhered to each other either partially or wholly.

A color film having a thermoplastic sheet laminated thereon is also available as the color sheet T. When a nonwoven fabric containing thermoplastic fibers such as polyethylene fibers or polypropylene fibers is used as the color sheet, it is possible to weld the color sheet together with the fibrous web W at the same time when the press-welded line portions H1, H2, . . . are formed in the fibrous web W as will be later described.

Figure 6:
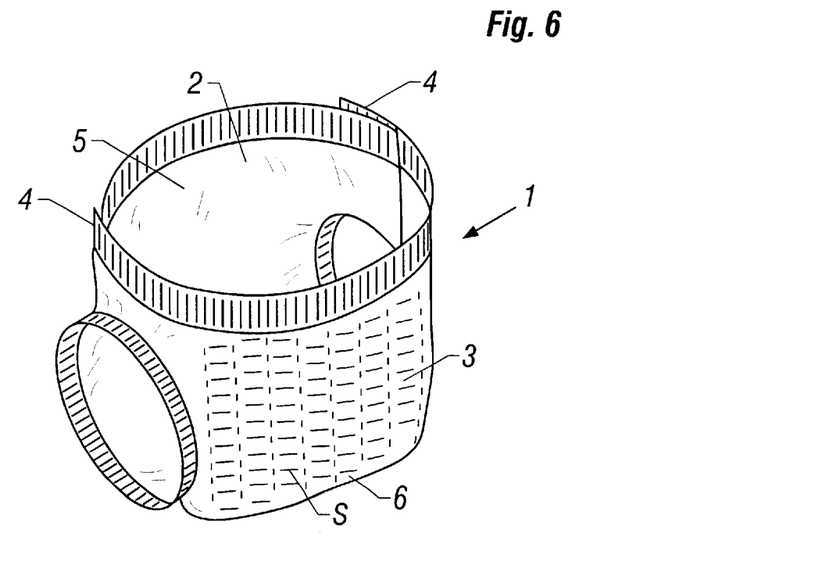
FIG. 6 is a perspective view of an open-type disposable diaper formed by using the nonwoven fabric of the present invention.

FIG. 6 illustrates a disposable diaper 1 for babies or little children as an example using the nonwoven fabric S.

The diaper 1 shown in FIG. 6 is called an "open-type diaper". The reverse portion 3 thereof is put on the bottom of babies. The front portion 2 is attached to the stomach of babies by being held between the legs. Overlap portions 4 of the reverse and front portions 3, 2 are adhered using an adhesive tape or a fastener.

In this diaper 1, a top sheet (inner sheet) 5 such as a nonwoven fabric or the like is disposed on the inner surface in contact with the user's skin, an absorbent is put on the outer surface thereof, and a back sheet (outer sheet) 6 is placed on the outer surface of the absorbent. In a diaper shown in FIG. 6, the nonwoven fabric S shown in FIG. 1 is overlaid as the back sheet 6 on the outer surface of an air-permeable and liquid-impermeable resin film (outer film).

Since the nonwoven fabric S which looks soft and feels soft is disposed on the outermost surface of this disposable diaper 1, one feels comfortable and has a touch close to that of underwear. Besides, as the figures such as "chick", "star", "flower" and the like are drawn on the outermost surface, this diaper has an appropriate appearance as a product for babies. Since the outer film and the nonwoven fabric S are adhered to each other using an adhesive, the air permeability of the resin film is not inhibited. Further, when using a product in which the color sheet T is adhered to the reverse surface of the nonwoven fabric S as shown in FIG. 5, the color of the color sheet T on the reverse surface is seen through the press-welded portions of the nonwoven fabric S, and the figure can easily be seen, providing an excellent appearance. When the color of the color sheet T is changed depending on sizes of diapers, the diapers of various sizes can be grouped according to the colors. In this case as well, the outer film and the color sheet T are adhered using an adhesive, so that the air permeability of the resin film is not inhibited.

In the press-welded line portions H1, H2, H3, . . . expressing the figures, the nonwoven fabric S is filmy and transparent or semitransparent. Accordingly, when the amount of urine absorbed into the diaper is increased, the color of urine is seen through the press-welded line portions H1, H2, H3, . . . , making it possible to observe the presence or absence of urine from outside the diaper. Especially when fibers having the cross-sectional shape shown in FIG. 4 are used as a starting material of the nonwoven fabric, the raised portions other than the press-welded line portions H1, H2, H3, . . . of the nonwoven fabric S become whiter, and give a sharper contract with the press-welded line portions H1, H2, H3, . . . which are filmy and transparent or semitransparent. Thus, the color of urine can easily be observed from outside the diaper.

The process for producing the nonwoven fabric S is described below.

This nonwoven fabric S can be produced by changing the shape of the projected portions of the hot roller in a conventional process for producing a nonwoven fabric.

First, thermoplastic short fibers which are fluffed by stretching and cutting a resin are sucked, and formed into a sheet on a conveyor to give a fibrous web W having a base weight of, for example, at least approximately 15 g/m$^2$ and at most 40 g/m$^2$.

Figure 7:
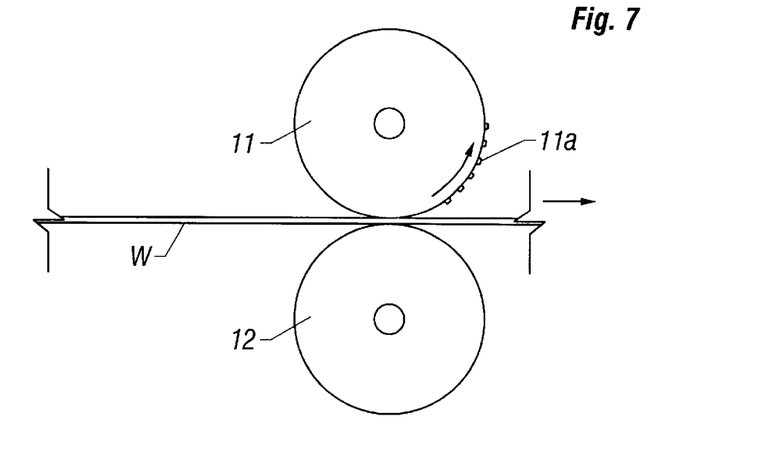
FIG. 7 is a front view illustrating a step of welding a nonwoven fabric using hot rollers.

This fibrous web W is partially welded using hot rollers. A roller 11 provided on the surface with projected portions 11a and a roller 12 having a smooth surface as shown in FIG. 7 are used as the hot rollers. A sheet (fibrous web W) formed of thermoplastic fibers is fed between the rollers 11 and 12 as shown in FIG. 8. At this time, the fibrous web W is partially pressed from one surface by means of the projected portions 11a of the hot roller 11 to hot-weld the thermoplastic resins of the fibrous web W. The press-welded line portions H1, H2, H3, . . . which are recessed in one surface of the fibrous web W and the press-welded dot portions Hd are thus formed. When the projected portions 11a on the surface of the hot roller 11 have the pattern shown in FIG. 1 or 2, the press-welded line portions H1, H2, H3, . . . and the press-welded dot portions Hd are formed in the resulting nonwoven fabric S.

When the color sheet T is adhered to the reverse surface of the nonwoven fabric S, a color resin film or a color nonwoven fabric containing thermoplastic fibers is laminated on the reverse surface of the fibrous web W, and the laminate is fed between the hot rollers 11 and 12 shown in FIGS. 7 and 8. When the press-welded line portions H1, H2, H3, . . . are formed in the fibrous web W by the projected portions 11a of the hot roller 11, the color resin film or the color nonwoven fabric and the fibrous web W are press-welded with each other in the press-welded line portions H1, H2, H3 . . . As a result, the nonwoven fabric S and the color sheet T can easily be adhered to each other, and the color can appear in the press-welded line portions.

The fibrous web W shown in FIG. 8 has two layers, namely a layer formed of dyed or colored fibers as an under layer, and an uncolored fibrous layer formed of fibers having the cross-sectional shape shown in, for example, FIG. 4(A), (B) or (C) as an upper layer. It is also possible that the two-layered fibrous web W is fed between the hot rollers 11 and 12 and the press-welded line portions H1, H2, H3, . . . are formed through the projected portions 11a. Then, the portions obtained by welding the fibers contained in the two layers become the press-welded portions. Since the press-welded portions come to be filmy, the color appears in the press-welded portions, and the sharp color contrast is given between the press-welded portions and the non-press-welded portions.

In the present invention, the press-welded line portions having a curved shape or a square shape are not necessarily continuous lines. For example, in FIG. 2, the press-welded line portion H1 drawing the contour of the "chick" may be an uncontinuous line (broken line), not a continuous line. The uncontinuous line refers to a line which is broken either partially or continuously.

As stated above, in the nonwoven fabric which is partially pressed and in which the thermoplastic fibers of the pressed portions are welded, the press-welded portions are formed into continuous line or uncontinuous line portions and dot portions, making it possible to obtain a highly bulky nonwoven fabric and give a soft impression to a user.

Further, the nonwoven fabric can have an excellent appearance unexpected from the conventional nonwoven fabric by drawing the pattern with the continuous line or uncontinuous line press-welded line portions.

Especially when the nonwoven fabric is formed of starting fibers having the square or uneven cross-sectional shape or the color resin sheet is overlaid under the nonwoven fabric, the figure drawn in the nonwoven fabric can be made much clearer.

What is claimed is:

1. A process for producing a nonwoven fabric comprising the following steps:
    a step of forming a fibrous web with short thermoplastic fibers, and
    a step of feeding and holding said fibrous web between a hot roller provided on the surface with projected portions and a hot roller having a smooth surface to form press-welded portions, which are recessed by the corresponding projected portions to be filmy, so that a nonwoven fabric is completed, and
    wherein a total area of the press-welded portions is at least 10% and at most 35% based on the area of the surface of the nonwoven fabric,
    wherein the fibers of the fibrous web are press-welded and melted in said press-welded portions, whereas the fibers of the fibrous web are not welded in the portions other than said press-welded portions,
    wherein the projected portions include: circular dot-shaped portions; and continuous or uncontinuous line-shaped portions, so that the corresponding press-welded portions formed on the nonwoven fabric include: dot-shaped press-welded portions; and continuous or uncontinuous line-shaped press-welded portions,
    wherein a total area of the dot-shaped press-welded portions is equal to or less than that of the continuous or uncontinuous line-shaped press-welded portions,
    wherein the continuous or uncontinuous line-shaped press-welded portions encircle portions of said nonwoven fabric to form a pattern of figures, characters or symbols containing at least curved portions or square portions, or a pattern of a combination thereof, and the dot-shaped press-welded portions, which are not a part of the pattern, are arranged inside and outside said encircled portions of said nonwoven fabric in order not to overlap with the continuous or uncontinuous line-shaped press-welded portions such that the continuous or uncontinuous line-shaped press-welded portions are spaced apart from a nearest adjacent dot-shaped press-welded portions at a space of at least 1 mm and at most 5 mm, wherein:
        the basis weight of the nonwoven fabric is 15 to 45 g/m$^2$, the specific volume of the press-welded portions is 3 to 10 cm$^3$/g and the specific volume of the non-press-welded portions is 10 to 30 cm$^3$/g, and
        the dot-shaped press-welded portions are distributed such that the volume ratio of the press-welded potions to the not welded portions is approximately fixed throughout the nonwoven fabric, and
        whereby the pattern formed solely by the continuous or uncontinuous line-shaped press-welded portions is clear because said dot-shaped press-welded portions do not overlap said continuous or uncontinuous line-shaped press-welded portions.

2. The process of producing a nonwoven fabric according to claim 1, wherein a fibrous web with no coloring added is laminated on a dyed or colored thermoplastic sheet, the laminate is held between both of the hot rollers, and the thermoplastic sheet and the fibrous web of the laminate are together press-welded with the projected portions of the hot roller to form press-welded portions.

3. The process according to claim 1, wherein a fibrous web formed of fibers without color added is laminated on a fibrous web formed of dyed or colored fibers, the thus-lated fibrous webs are held between both of the hot rollers, and the colored fibrous web and the fibrous web without color added are partially press-welded together with the projected portions of the hot roller to form press-welded portions.

4. The process of producing a nonwoven fabric according to claim 1, wherein the thermoplastic fibers have a fiber length of at least 30 mm and at most 70 mm.

* * * * *